(12) United States Patent
Nakano et al.

(10) Patent No.: US 10,207,245 B2
(45) Date of Patent: Feb. 19, 2019

(54) VOLTAGE APPLICATION DEVICE AND DISCHARGE DEVICE

(71) Applicant: PANASONIC INTELLECTUAL PROPERTY MANAGEMENT CO., LTD., Osaka (JP)

(72) Inventors: Yukari Nakano, Shiga (JP); Itaru Saida, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/684,364

(22) Filed: Aug. 23, 2017

(65) Prior Publication Data

US 2018/0065104 A1   Mar. 8, 2018

(30) Foreign Application Priority Data

Sep. 8, 2016  (JP) .................................. 2016-175902

(51) Int. Cl.
| | | |
|---|---|---|
| *B01J 19/08* | (2006.01) | |
| *H01T 19/00* | (2006.01) | |
| *A61L 9/04* | (2006.01) | |
| *A61L 9/14* | (2006.01) | |
| *A61L 9/12* | (2006.01) | |

(Continued)

(52) U.S. Cl.
CPC ............. *B01J 19/088* (2013.01); *A61L 9/046* (2013.01); *A61L 9/12* (2013.01); *A61L 9/14* (2013.01); *B05B 5/005* (2013.01); *B05B 5/10* (2013.01); *H01T 19/00* (2013.01); *A61L 2209/212* (2013.01); *A61L 2209/213* (2013.01); *B01J 2219/0801* (2013.01); *B01J 2219/0849* (2013.01); *B01J 2219/0877* (2013.01)

(58) Field of Classification Search
None
See application file for complete search history.

(56) References Cited

U.S. PATENT DOCUMENTS

| | | | |
|---|---|---|---|
| 2012/0126041 A1 | 5/2012 | Nunomura et al. | |
| 2014/0162198 A1* | 6/2014 | Krichtafovitch ...... | F23C 99/001 431/2 |
| 2014/0255855 A1* | 9/2014 | Krichtafovitch ........ | F23N 5/00 431/2 |

FOREIGN PATENT DOCUMENTS

| | | |
|---|---|---|
| EP | 1445026 A1 | 8/2004 |
| JP | 2011-067738 A | 4/2011 |

(Continued)

OTHER PUBLICATIONS

The Extended European Search Report dated Jan. 8, 2018 for the related European Patent Application No. 17185428.4.

*Primary Examiner* — Kishor Mayekar
(74) *Attorney, Agent, or Firm* — McDermott Will & Emery LLP

(57) ABSTRACT

A voltage application device according to the present disclosure includes a voltage application circuit and a control circuit. The control circuit causes the voltage application circuit to alternately repeat a first mode and a second mode. The first mode is a mode that raises a voltage while time elapses, and generates a discharge current by promoting corona discharge to dielectric breakdown. The second mode is a mode that lowers the voltage to cut off the discharge current by causing a load to be in an overload state against the voltage application circuit. This can suppress an amount of ozone generated, while increasing an amount of radicals produced.

8 Claims, 7 Drawing Sheets

(51) Int. Cl.
    *B05B 5/00*         (2006.01)
    *B05B 5/10*         (2006.01)

(56)        References Cited

FOREIGN PATENT DOCUMENTS

WO      2004/051689 A1      6/2004
WO      2013/080686 A1      6/2013
WO      2014/128477 A1      8/2014

* cited by examiner

VOLTAGE APPLICATION DEVICE AND DISCHARGE DEVICE

RELATED APPLICATIONS

This application claims the benefit of Japanese Application No. 2016-175902, filed on Sep. 8, 2016, the entire disclosure of which Application is incorporated by reference herein.

BACKGROUND

1. Technical Field

The present disclosure generally relates to a voltage application device and discharge device. More specifically, the present disclosure relates to a voltage application device and a discharge device, which apply a voltage to a load including a discharge electrode to generate discharge.

2. Description of the Related Art

Unexamined Japanese Patent Publication No. 2011-67738 proposes a discharge device including a discharge electrode and a voltage application circuit (electric power supply unit).

In this kind of discharge device, the voltage application circuit applies a voltage to the discharge electrode, thereby generating corona discharge. Liquid is supplied to the discharge electrode, and then electrostatic atomization is achieved during the discharge, thereby producing charged fine particulate liquid including radicals as an active ingredient. The charged fine particulate liquid including the radicals exerts advantageous effects such as sterile filtration and odor elimination.

Incidentally, in the discharge device, introduced energy is preferably increased to increase an amount of radicals produced that eventually exerts various advantageous effects. However, in the above-described conventional discharge device, when the introduced energy is merely increased, the amount of radicals produced is increased, but an amount of unnecessary ozone generated may also be increased.

SUMMARY

The present disclosure is made in consideration of such a circumstance, and an object of the present disclosure is to provide a voltage application device and a discharge device capable of suppressing increase in an amount of ozone generated, while increasing an amount of radicals produced.

A voltage application device of a first aspect includes a voltage application circuit and a control circuit. The voltage application circuit is configured to apply a voltage to a load including a discharge electrode to cause the discharge electrode to discharge. The control circuit is configured to control the voltage application circuit based on a monitoring target including at least one of an output current and an output voltage of the voltage application circuit. The control circuit causes the voltage application circuit to alternately repeat a first mode and a second mode. The first mode is a mode that raises the voltage while time elapses, and generates a discharge current by promoting corona discharge to dielectric breakdown. The second mode is a mode that lowers the voltage to cut off the discharge current by causing the load to be in an overload state against the voltage application circuit. The control circuit causes the voltage application circuit to operate in the first mode when magnitude of the monitoring target is less than a threshold, and causes the voltage application circuit to operate in the second mode when the magnitude of the monitoring target is not less than the threshold.

In the first aspect, the voltage application device of a second aspect further includes a time adjuster that adjusts a length of a discharge period, and the dielectric breakdown is periodically generated at the discharge period.

In the second aspect, the voltage application device of a third aspect includes an isolation transformer, and is configured to boost an input voltage that is input to a primary side of the isolation transformer, and to apply the voltage to the load that is electrically connected to a secondary side of the isolation transformer. The time adjuster is disposed on the primary side of the isolation transformer.

In the second or third aspect, the voltage application device of a fourth aspect further includes an operation unit for receiving an operation performed by a user, and the time adjuster is configured to adjust the length of the discharge period in accordance with the operation to the operation unit performed by the user.

In the second or third aspect, the voltage application device of a fifth aspect is configured such that the time adjuster is configured to automatically adjust the length of the discharge period in accordance with an output of a sensor that detects a condition around the discharge electrode.

A discharge device of a sixth aspect includes the voltage application device of any one of aspects 1 to 5 and the discharge electrode.

In the sixth aspect, the discharge device of a seventh aspect further increases a liquid supply unit that supplies liquid to the discharge electrode, and the liquid is electrostatically atomized by the discharge.

In the sixth or seventh aspect, the discharge device of an eighth aspect further includes an opposite electrode disposed so as to face the discharge electrode via a gap. The discharge device is configured such that the dielectric breakdown is intermittently generated between the discharge electrode and the opposite electrode by applying the voltage between the discharge electrode and the opposite electrode.

The present disclosure has an advantageous effect capable of suppressing increase in an amount of ozone generated, while increasing an amount of radicals produced.

DETAILED DESCRIPTION

First Exemplary Embodiment (1) Outline

Figure 1:
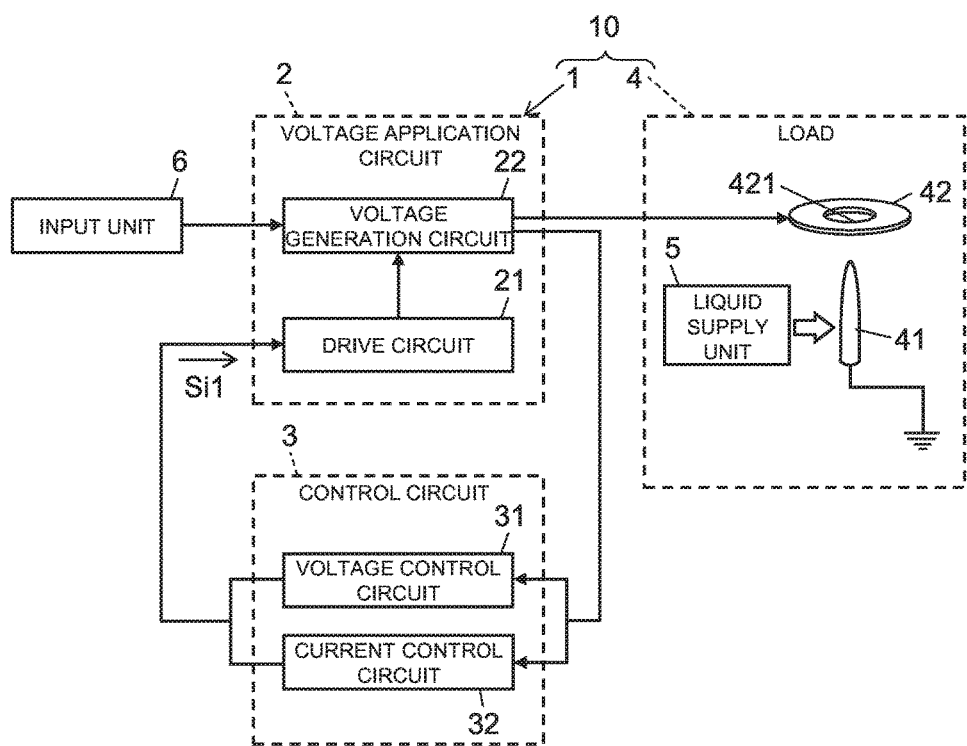
FIG. 1 is a block diagram illustrating a discharge device according to a first exemplary embodiment.

As illustrated in FIG. 1, voltage application device 1 according to the present exemplary embodiment includes voltage application circuit 2 and control circuit 3. Voltage application device 1 is a device causing discharge electrode 41 to perform a discharge by applying a voltage to load 4 including discharge electrode 41.

Further, as illustrated in FIG. 1, discharge device 10 according to the present exemplary embodiment includes voltage application device 1, discharge electrode 41, load 4 including opposite electrode 42 disposed so as to face discharge electrode 41, and liquid supply unit 5 that supplies liquid to discharge electrode 41. More specifically, discharge device 10 includes voltage application circuit 2, control circuit 3, liquid supply unit 5, discharge electrode 41, and opposite electrode 42 as components thereof. However, discharge device 10 may include at least voltage application device 1 and discharge electrode 41 as components thereof, and may not include opposite electrode 42 and liquid supply unit 5 as components thereof.

Voltage application circuit 2 applies a voltage to load 4 (hereafter, a voltage applied to load 4 is also referred to as an "apply voltage"). This causes discharge at discharge electrode 41 included in load 4. Control circuit 3 controls voltage application circuit 2. Control circuit 3 controls voltage application circuit 2, based on a monitoring target. The "monitoring target" herein includes at least one of an output current and an output voltage of voltage application circuit 2.

Control circuit 3 causes voltage application circuit 2 to alternately repeat a first mode and a second mode. In other words, operation modes of voltage application circuit 2 include two modes that are the first mode and the second mode, and control circuit 3 causes voltage application circuit 2 to alternately repeat those two operation modes. The first mode is a mode that raises the apply voltage while time elapses, and generates a discharge current by promoting corona discharge to dielectric breakdown. The second mode is a mode that lowers the apply voltage to cut off the discharge current by causing load 4 to be in an overload state against voltage application circuit 2. The "discharge current" herein means a relatively large current that is generated after the dielectric breakdown, and does not mean a minute current of several μA that is generated in the corona discharge before the dielectric breakdown. The "overload state" herein is a state in which a load not less than a tolerable amount is applied to voltage application circuit 2, more specifically, a state in which the discharge current cannot be maintained due to the lowered apply voltage.

Furthermore, control circuit 3 causes voltage application circuit 2 to operate in the first mode when magnitude of the monitoring target is less than a threshold, and causes voltage application circuit 2 to operate in the second mode when the magnitude of the monitoring target is not less than the threshold. In other words, voltage application circuit 2 operates in the first mode that raises the apply voltage while time elapses until the magnitude of the monitoring target reaches the threshold. At this time, at discharge electrode 41, the corona discharge is promoted to the dielectric breakdown and the discharge current is generated. When the magnitude of the monitoring target reaches the threshold, voltage application circuit 2 operates in the second mode that lowers the apply voltage. At this time, load 4 enters the overload state against voltage application circuit 2 and then the discharge current is cut off. In other words, since load 4 enters the overload state, voltage application circuit 2 cannot maintain the discharge current, and therefore the discharge current naturally disappears (fades away).

As a result, in discharge device 10 according to the present exemplary embodiment, when the apply voltage is raised and then the dielectric breakdown is attained, a relatively large discharge current instantaneously flows, and immediately after that, the apply voltage is lowered and the discharge current is cut off. Then, the apply voltage is raised and thus the dielectric breakdown is attained again. Such a phenomenon is repeated. Discharge in such a form that the phenomenon in which the corona discharge is promoted to the dielectric breakdown is intermittently repeated is referred to as "leader discharge" hereafter. That is, in discharge device 10, a discharge path is intermittently formed around discharge electrode 41 by the leader discharge, thereby repeatedly generating a pulsed discharge current. The leader discharge will be explained in detail in a section of "(2.2) Leader Discharge".

This leader discharge generates radicals by using large energy in comparison with the corona discharge. A large amount of radicals that is about twice to 10 times larger than that in the corona discharge is generated. The radicals generated in this manner exert useful effects in various scenes, in addition to sterile filtration, odor elimination, moisture keeping, freshness keeping, and virus inactivation. Here, when the radicals are produced by the leader discharge, ozone is also generated. However, although the leader discharge produces about twice to 10 times radicals larger than those produced in the corona discharge, an amount of ozone generated is suppressed to the same amount as that generated in the corona discharge. Therefore, in voltage application device 1 according to the present exemplary embodiment and discharge device 10 provided with the same, the amount of ozone generated can be suppressed, while increasing the amount of radicals produced.

(2) Detailed Description

Hereinafter, voltage application device 1 according to the present exemplary embodiment and discharge device 10 will be described in more detail.

(2.1) Entire Configuration

Discharge device 10 according to the present exemplary embodiment includes voltage application circuit 2, control circuit 3, load 4, and liquid supply unit 5, as illustrated in FIG. 1. Load 4 includes discharge electrode 41 and opposite electrode 42. Liquid supply unit 5 supplies liquid to discharge electrode 41. Discharge device 10 according to the present exemplary embodiment applies a voltage to load 4 from voltage application circuit 2, in a state in which the liquid is supplies to discharge electrode 41. This generates a discharge at least at discharge electrode 41, and the liquid retained at discharge electrode 41 is electrostatically atomized by the discharge. That is, discharge device 10 according to the present exemplary embodiment configures a so-called electrostatic atomization device.

Discharge electrode 41 is a stick-shaped electrode. Discharge electrode 41 includes a distal end part at one end in a longitudinal direction, and includes a base end part at the other end (an end opposite to the distal end part) in the longitudinal direction. Discharge electrode 41 is a needle electrode in which the distal end part is formed into a taper shape. The "taper shape" herein is not limited to a shape having a highly sharpened distal end, and includes a shape having a rounded distal end.

Opposite electrode 42 is disposed so as to face the distal end part of discharge electrode 41. Opposite electrode 42 is, for example, plate-shaped, and is formed into a ring shape having opening 421 in its center. Opening 421 penetrates opposite electrode 42 in a thickness direction of opposite electrode 42. Here, a positional relationship between opposite electrode 42 and discharge electrode 41 is determined such that the thickness direction of opposite electrode 42 (a penetrating direction of opening 421) coincides with the longitudinal direction of discharge electrode 41, and the distal end part of discharge electrode 41 is positioned near the center of opening 421 of opposite electrode 42. That is, a gap (space) is left by at least opening 421 of opposite electrode 42 between opposite electrode 42 and discharge electrode 41. In other words, opposite electrode 42 is disposed so as to face discharge electrode 41 via the gap, and therefore opposite electrode 42 is electrically insulated from discharge electrode 41.

Liquid supply unit 5 supplies liquid to be electrostatically atomized to discharge electrode 41. Liquid supply unit 5 is configured by, for example, a cooling device that cools discharge electrode 41 to produce dew condensation water at discharge electrode 41. More specifically, liquid supply unit 5 is disposed so as to come into contact with the base end part of discharge electrode 41, and cools entire discharge electrode 41 through the base end part. Moisture in the air is then condensed and adheres to a surface of discharge electrode 41 as the dew condensation water. In this configuration, liquid supply unit 5 can supply liquid (dew condensation water) to discharge electrode 41 by using the moisture in the air, thereby eliminating supply and refilling of liquid to discharge device 10.

Voltage application circuit 2 includes drive circuit 21 and voltage generation circuit 22. Drive circuit 21 is a circuit for driving voltage generation circuit 22. Voltage generation circuit 22 is a circuit that receives power supply from input unit 6 and generates the voltage to be applied to load 4 (apply voltage). Input unit 6 is a power supply circuit that generates a direct-current (DC) voltage of about several V to more than ten V. In the present exemplary embodiment, the description is made assuming that input unit 6 is not included in components of voltage application device 1, but input unit 6 may be included in the components of voltage application device 1. Specific circuit configurations of drive circuit 21 and voltage generation circuit 22 will be explained in a section of "(2.3) Circuit Configuration".

Figure 3:
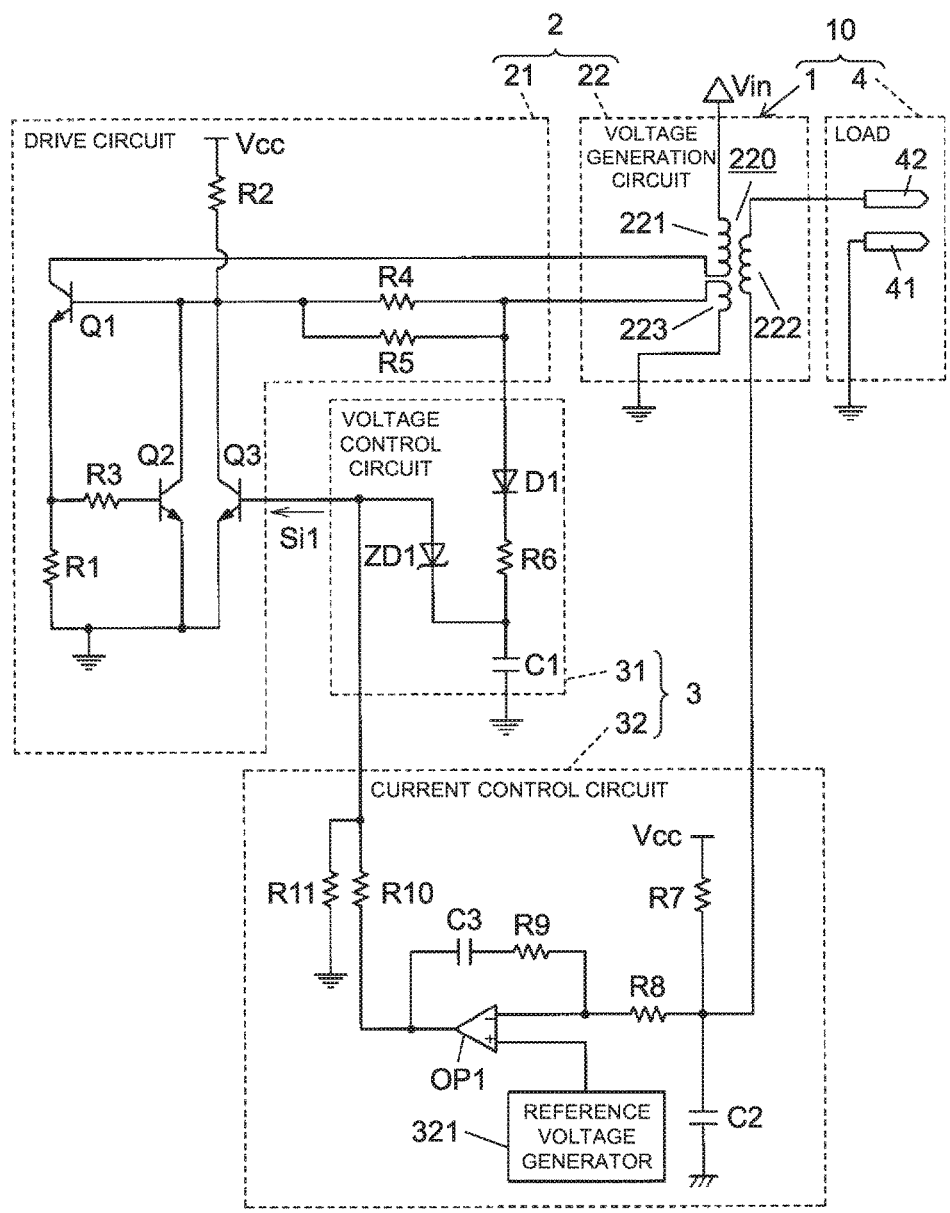
FIG. 3 is a circuit diagram illustrating an example of the discharge device.

Voltage application circuit 2 is electrically connected to load 4 (discharge electrode 41 and opposite electrode 42) (refer to FIG. 3). Voltage application circuit 2 applies a high voltage to load 4. Here, voltage application circuit 2 applies the high voltage between discharge electrode 41 that acts as a negative electrode (ground) and opposite electrode 42 that acts as a positive electrode (plus). In other words, in a state in which voltage application circuit 2 applies the high voltage to load 4, a potential difference is generated between discharge electrode 41 and opposite electrode 42. At this time, opposite electrode 42 has a high potential and discharge electrode 41 has a low potential. The "high voltage" herein may be a voltage set so as to cause discharge electrode 41 to produce the leader discharge, and is a voltage whose peak is, for example, about 7.0 kV. However, the high voltage applied from voltage application circuit 2 to load 4 is not limited to about 7.0 kV, and is appropriately set according to, for example, shapes of discharge electrode 41 and opposite electrode 42, a distance between discharge electrode 41 and opposite electrode 42, or other factors.

Here, the operation modes of voltage application circuit 2 include two modes, that is, the first mode and the second mode, as described above. In the first mode, voltage application circuit 2 raises the apply voltage while time elapses, and generates the discharge current by promoting the corona discharge to the dielectric breakdown. In the second mode, voltage application circuit 2 lowers the apply voltage to cut off the discharge current by causing load 4 to be in an overload state against voltage application circuit 2.

Control circuit 3 includes voltage control circuit 31 and current control circuit 32. Voltage control circuit 31 controls drive circuit 21 of voltage application circuit 2, based on the monitoring target including the output voltage of voltage application circuit 2. Control circuit 3 outputs control signal Si1 to drive circuit 21, and controls drive circuit 21 by using control signal Si1. Current control circuit 32 controls drive circuit 21 of voltage application circuit 2, based on the monitoring target including the output current of voltage application circuit 2. That is, in the present exemplary embodiment, control circuit 3 monitors both the output current and the output voltage of voltage application circuit 2, to control voltage application circuit 2. However, there is a correlation between the output voltage (secondary-side voltage) of voltage application circuit 2 and a primary-side voltage of voltage application circuit 2, and therefore voltage control circuit 31 may indirectly detects the output current of voltage application circuit 2 from the primary-side voltage of voltage application circuit 2. Similarly, there is a correlation between the output current (secondary-side current) of voltage application circuit 2 and an input current (primary-side current) of voltage application circuit 2, and therefore current control circuit 32 may indirectly detects the output current of voltage application circuit 2 from the input current of voltage application circuit 2. Specific circuit configurations of voltage control circuit 31 and current control circuit 32 will be explained in a section of "(2.3) Circuit Configuration".

Control circuit 3 causes voltage application circuit 2 to operate in the first mode when magnitude of the monitoring target is less than a threshold, and causes voltage application circuit 2 to operate in the second mode when the magnitude of the monitoring target is not less than the threshold. With this configuration, voltage application circuit 2 operates so as to alternately repeat the first mode and the second mode. Then, at discharge electrode 41, the leader discharge that is the phenomenon in which the corona discharge is promoted to the dielectric breakdown is intermittently repeated is produced.

In a further detailed description, discharge device 10 first generates local corona discharge at the distal end part of discharge electrode 41 (in a strict sense, at a distal end part of the liquid retained at the distal end part). In the present exemplary embodiment, since discharge electrode 41 is the negative electrode (ground), the corona discharge generated at the distal end part of discharge electrode 41 includes coronas having a negative polarity. Discharge device 10 further promotes the corona discharge generated at discharge electrode 41 to discharge having high energy. Due to this discharge having high energy, the dielectric breakdown (entire path breakdown) is produced around discharge electrode 41, and a discharge path is formed around discharge electrode 41. In discharge device 10 according to the present exemplary embodiment, voltage application circuit 2 alternately repeats the first mode and the second mode, thereby intermittently generating the dielectric breakdown between discharge electrode 41 and opposite electrode 42, and intermittently forming the discharge path that connects discharge electrode 41 and opposite electrode 42.

Figure 2:
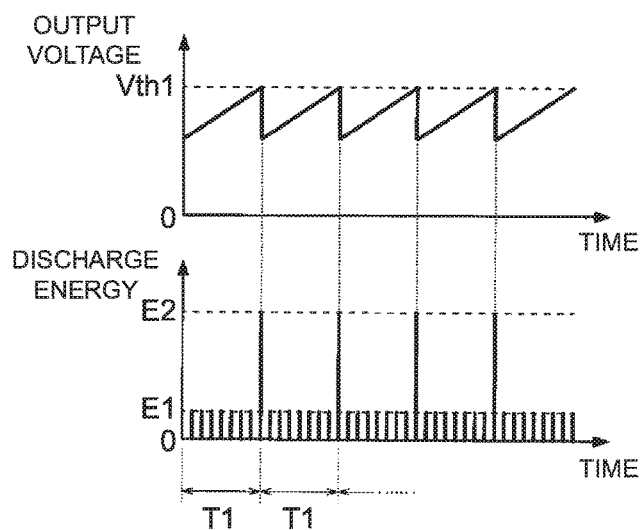
FIG. 2 is a graph schematically illustrating a form of discharge of the discharge device.

In the leader discharge, a discharge current that is about twice to 10 times larger than that in the corona discharge flows through the discharge path between discharge electrode 41 and opposite electrode 42. Therefore, as illustrated in FIG. 2, a minute current caused by the corona discharge flows until the apply voltage reaches threshold Vth1. When the apply voltage reaches threshold Vth1, the dielectric breakdown is generated and a relatively large discharge current instantaneously flows. In FIG. 2, with a horizontal axis as a time axis, the output voltage of voltage application circuit 2 (apply voltage) is illustrated in an upper stage, and discharge energy is illustrated in a lower stage. The "discharge energy" herein is discharge energy generated in load 4, and has a substantially proportional relation with the discharge current. That is, in a period in which the apply voltage is raised to generate the dielectric breakdown, a minute current whose discharge energy is "E1" is generated by the corona discharge. When the apply voltage reaches threshold Vth1, the dielectric breakdown is generated and discharge with high energy whose discharge energy is "E2" (>E1) is generated.

Here, when a value of threshold Vth1 is constant, and a raising rate of the apply voltage is also constant, a period of generation of the dielectric breakdown (hereafter, also referred to as "discharge period") in the leader discharge is substantially constant. In an example in FIG. 2, the dielectric breakdown is periodically generated at discharge period T1. Discharge period T1 is equal to a period in which the apply voltage reaches threshold Vth1, that is, a period in which the operation mode of voltage application circuit 2 is switched from the first mode to the second mode.

In discharge device 10 according to the present exemplary embodiment, voltage application circuit 2 applies the voltage to load 4, in a state in which the liquid (dew condensation water) is supplied (retained) at discharge electrode 41. Therefore, in load 4, due to the potential difference between discharge electrode 41 and opposite electrode 42, discharge (leader discharge) is produced between discharge electrode 41 and opposite electrode 42. At this time, the liquid retained at discharge electrode 41 is electrostatically atomized by the discharge. As a result, in discharge device 10, charged fine particulate liquid in which each particulate is nanometer-sized and radicals are contained is produced. The produced charged fine particulate liquid is released to a periphery of discharge device 10 through, for example, opening 421 of opposite electrode 42.

(2.2) Leader Discharge

Subsequently, the leader discharge will be explained in more detail.

In general, when energy is introduced between a pair of electrodes to generate discharge, a form of discharge is promoted from corona discharge to glow discharge or arc discharge, according to an amount of introduced energy.

The corona discharge is locally generated at one electrode, and does not accompany dielectric breakdown between a pair of electrodes. The glow discharge and the arc discharge accompany the dielectric breakdown between the pair of electrodes. In the glow discharge and the arc discharge, in a period in which energy is introduced between the pair of electrodes, a discharge path formed by the dielectric breakdown is maintained, and therefore a discharge current is continuously generated between the pair of electrodes.

In contrast, although the leader discharge accompanies the dielectric breakdown between the pair of electrodes, the dielectric breakdown is generated not continuously but intermittently. Therefore, a discharge current generated between the pair of electrodes is also intermittently generated.

As an example, a discharge frequency in the leader discharge (a reciprocal of the discharge period) is about 50 Hz to 10 kHz, and a pulse width of the discharge current (duration of the discharge current) is about 200 ns. In this manner, the leader discharge is different from the glow discharge and the ark discharge in which the dielectric breakdown is continuously generated (that is, the discharge current is continuously generated) in that a state of high discharge energy and a state of low discharge energy are repeated.

Although the leader discharge produces a large amount of radicals about twice to 10 times as large as that in the corona discharge, an amount of ozone generated is suppressed to the same amount as that in the corona discharge. This is considered to be because, when the ozone generated by the leader discharge is released, a part of ozone generated is broken by being exposed to the leader discharge having high energy.

(2.3) Circuit Configuration

Subsequently, a specific circuit configuration of voltage application device 1 will be described with reference to FIG. 3. FIG. 3 is a circuit diagram schematically illustrating an example of a circuit configuration of discharge device 10, and illustration of input unit 6 is omitted in FIG. 3.

As described above, voltage application circuit 2 includes drive circuit 21 and voltage generation circuit 22. In an example in FIG. 3, voltage application circuit 2 is an insulation-type DC/DC converter that boosts input voltage Vin (for example, 13.8 V) from input unit 6, and outputs the boosted voltage as an output voltage. The output voltage of voltage application circuit 2 is applied to load 4 (discharge electrode 41 and opposite electrode 42) as the apply voltage.

Voltage generation circuit 22 includes isolation transformer 220 including primary winding 221, secondary winding 222, and auxiliary winding 223. Primary winding 221 and auxiliary winding 223 are electrically isolated from secondary winding 222, and are magnetically combined with secondary winding 222. Opposite electrode 42 is electrically connected to an end of secondary winding 222.

Drive circuit 21 includes transistor Q1, and is configured to supply power to primary winding 221 of isolation transformer 220 by switching operation of transistor Q1. Drive circuit 21 includes transistor Q2, transistor Q3, and resisters R1 to R5, in addition to transistor Q1. Transistors Q1, Q2, and Q3 each are configured by an npn-type bipolar transistor, for example.

A collector of transistor Q1 is connected to primary winding 221 and an emitter of transistor Q1 is connected to the ground via resister R1. A series circuit of primary winding 221, transistor Q1, and resister R1 is applied with input voltage Vin from input unit 6. A base of transistor Q1 is connected to control power supply Vcc via resister R2. Control power supply Vcc applies a control voltage (for example, 5.1 V) to drive circuit 21.

Collectors of transistors Q2 and Q3 are connected to the base of transistor Q1. Emitters of transistors Q2 and Q3 are connected to the ground. A base of transistor Q2 is connected to the emitter of transistor Q1 via resister R3. The base of transistor Q1 is connected to an end of auxiliary winding 223 via a parallel circuit of resisters R4 and R5. The other end of auxiliary winding 223 is connected to the ground. A base of transistor Q3 is connected to control circuit 3 (voltage control circuit 31 and current control circuit 32) to input control signal Si1 from control circuit 3.

With the above-described configuration, voltage application circuit 2 configures a self-excited converter. That is, when transistor Q1 is turned on and then a current flows in primary winding 221 of isolation transformer 220, a voltage across resister R1 is raised and transistor Q2 is turned on. Accordingly, the base of transistor Q1 is connected to the ground via transistor Q2, and therefore transistor Q1 is turned off. When transistor Q1 is turned off, the current flowing in primary winding 221 is cut off. Then the voltage across resister R1 is lowered and then transistor Q2 is turned off. Accordingly, a high voltage is induced at secondary winding 222 of isolation transformer 220, and is applied to load 4 as the output voltage of voltage application circuit 2. At this time, a voltage is also induced at auxiliary winding 223 by the induced voltage generated at secondary winding 222. Then a voltage between the base and emitter of transistor Q1 is raised and then transistor Q1 is turned on. Voltage application circuit 2 repeats the above-described operation, thereby boosting input voltage Vin and applying the output voltage to load 4.

Control circuit 3 includes voltage control circuit 31 and current control circuit 32 as described above.

Voltage control circuit 31 includes diode D1, resister R6, capacitor C1, and Zener diode ZD1. An anode of diode D1 is connected to a connecting point of auxiliary winding 223 and resisters R4 and R5. A cathode of diode D1 is connected to one end of capacitor C1 via resister R6. The other end of capacitor C1 is connected to the ground. Further, a cathode of Zener diode ZD1 is connected to the one end (connecting point with resister R6) of capacitor C1. An anode of Zener diode ZD1 is connected to the base of transistor Q3 as an output terminal of voltage control circuit 31.

With the above-described configuration, voltage control circuit 31 monitors the induced voltage at auxiliary winding 223, thereby indirectly monitoring the output voltage (induced voltage at secondary winding 222) of voltage application circuit 2 that is the monitoring target. In other words, while the output voltage of voltage application circuit 2 is less than threshold Vth1, Zener diode ZD1 of voltage control circuit 31 is in an off state. On the other hand, when the output voltage of voltage application circuit 2 is not less than threshold value Vth1, Zener diode ZD1 of voltage control circuit 31 is turned on. At this time, control signal Si1 exceeds control threshold Sth1 (refer to FIG. 4), a voltage is applied to between the base and the emitter of transistor Q3 and then transistor Q3 is turned on. Accordingly, a base current of transistor Q1 flows into the ground via transistor Q3, thereby reducing a collector current of transistor Q1. Therefore, when the output voltage of voltage application circuit 2 is not less than threshold Vth1, energy introduced from drive circuit 21 of voltage application circuit 2 to voltage generation circuit 22 is reduced.

Current control circuit 32 includes an operational amplifier OP1, reference voltage generator 321, resisters R7 to R11, and capacitors C2 and C3. One end of capacitor C2 is connected to control power supply Vcc via resister R7. The other end of capacitor C2 is connected to the ground. Control power supply Vcc applies the control voltage (for example, 5.1 V) to a series circuit of resister R7 and capacitor C2. A connecting point (the one end of capacitor C2) of resister R7 and capacitor C2 is connected to an inverting input terminal of operational amplifier OP1 via resister R8. An end part (the other end) on an opposite side to opposite electrode 42 of secondary winding 222 of isolation transformer 220 is connected to the connecting point (the one end of capacitor C2) of resister R7 and capacitor C2. In other words, control power supply Vcc is connected to opposite electrode 42 via resister R7 and secondary winding 222. Reference voltage generator 321 is connected to a non-inverting input terminal of operational amplifier OP1, and inputs a reference voltage to the terminal. A series circuit of resister R9 and capacitor C3 is connected between the non-inverting input terminal and an output terminal of operational amplifier OP1. An end of resister R10 is connected to the output terminal of operational amplifier OP1. The other end of resister R10 is connected to the ground via resister R11. A connecting point of resister R10 and resister R11 (the other end of resister R10) is connected to the base of transistor Q3 as an output terminal of current control circuit 32.

With the above-described configuration, current control circuit 32 monitors an induced current at secondary winding 222, thereby monitoring the output current (induced voltage at secondary winding 222) of voltage application circuit 2 that is the monitoring target. That is, while the output current of voltage application circuit 2 is less than the threshold, an output of operational amplifier OP1 of current control circuit 32 is a low (L) level. When the output current of voltage application circuit 2 is not less than the threshold, the output of operational amplifier OP1 of current control circuit 32 becomes a high (H) level. At this time, control signal Si1 exceeds control threshold Sth1 (refer to FIG. 4), the voltage is applied to between the base and the emitter of transistor Q3 and then transistor Q3 is turned on. Accordingly, the base current of transistor Q1 flows into the ground via transistor Q3, thereby reducing the collector current of transistor Q1. Therefore, when the output current of voltage application circuit 2 is not less than the threshold, current control circuit 32 reduces energy introduced from drive circuit 21 of voltage application circuit 2 to voltage generation circuit 22.

(2.4) Operation

With the circuit configuration illustrated in FIG. 3, in discharge device 10, control circuit 3 operates in a manner described below, and therefore the leader discharge is produced between discharge electrode 41 and opposite electrode 42.

In other words, control circuit 3 monitors the output voltage of voltage application circuit 2 as the monitoring target until the dielectric breakdown is generated. When the monitoring target (output voltage) reaches the value not less than threshold Vth1, control circuit 3 causes voltage control circuit 31 to reduce the energy introduced to voltage generation circuit 22. On the other hand, control circuit 3 monitors the output current of voltage application circuit 2 as the monitoring target after the dielectric breakdown is generated. When the monitoring target (output current) reaches the value not less than a threshold, control circuit 3 causes current control circuit 32 to reduce the energy introduced to voltage generation circuit 22. Thus, voltage application circuit 2 operates in the second mode that lowers the apply voltage to cut off the discharge current by causing load 4 to be in the overload state against voltage application circuit 2. That is, the operation mode of voltage application circuit 2 is switched from the first mode to the second mode.

At this time, since both the output voltage and the output current of voltage application circuit 2 are reduced, control circuit 3 restarts the switching operation of drive circuit 21. Thus, voltage application circuit 2 operates in the first mode that raises the apply voltage while time elapses, and generates a discharge current by promoting the corona discharge to the dielectric breakdown. That is, the operation mode of voltage application circuit 2 is switched from the second mode to the first mode.

Figure 4:
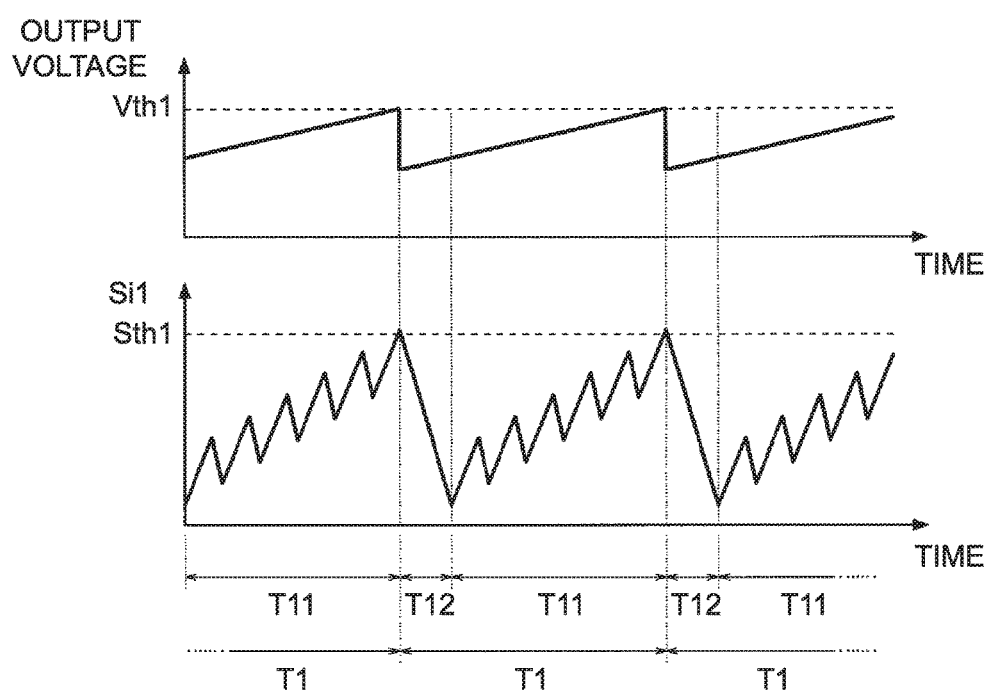
FIG. 4 is a graph schematically illustrating a form of discharge of the discharge device.

In FIG. 4, with a horizontal axis representing a time axis, the output voltage of voltage application circuit 2 (apply voltage) is illustrated in the upper stage, and control signal Si1 is illustrated in the lower stage. In FIG. 4, a period in which voltage application circuit 2 operates in the first mode is denoted by "T11", and a period in which voltage application circuit 2 operates in the second mode is denoted by "T12". In other words, during period T11 in which the output voltage of voltage application circuit 2 reaches threshold Vth1, voltage application circuit 2 operates in the first mode, and control signal Si1 that is the output of control circuit 3 is gradually raised. Here, in the example in FIG. 4, repetition of increase and decrease in control signal Si1 during period T11 schematically represents fluctuation in the output of voltage control circuit 31 (control signal Si1) due to the induced voltage at auxiliary winding 223. When control signal Si1 exceeds control threshold Sth1, the operation mode of voltage application circuit 2 is switched from the first mode to the second mode, and the output voltage of voltage application circuit 2 is lowered. During period T12 in which voltage application circuit 2 operates in the second mode, control signal Si1 that is the output of control circuit 3 is gradually lowered.

At this time, after current control circuit 32 operates, that is, the output of operational amplifier OP1 becomes a H level, the raising rate of the output voltage (apply voltage) of voltage application circuit 2 is determined by an effect of an integration circuit including operational amplifier OP1, resister R9, and capacitor C3. In short, in the example in FIG. 4, an inclination of the output voltage during discharge period T1 is determined by a time constant of the integration circuit including operational amplifier OP1, resister R9, and capacitor C3. In other words, discharge period T1 is determined by the time constant of the integration circuit including operational amplifier OP1, resister R9, and capacitor C3.

Control circuit 3 repeats the above-described operation, and therefore voltage application circuit 2 operates so as to alternately repeat the first mode and the second mode. That is, period T11 and period T12 in FIG. 4 are alternately repeated. As a result, at discharge electrode 41, the leader discharge is produced. In the leader discharge, the phenomenon in which the corona discharge is promoted to the dielectric breakdown is intermittently repeated.

(3) Modifications

Discharge device 10 according to the first exemplary embodiment is merely an example of the present disclosure, and the present disclosure is not limited to discharge device 10 described above. Various modifications can be made depending on the design within a scope of technical ideas according to the present disclosure. Hereinafter, modifications of the first exemplary embodiment will be listed.

Discharge device 10 may omit liquid supply unit 5 for generating the charged fine particulate liquid. In this case, discharge device 10 produces air ions as an active ingredient by the leader discharge produced between discharge electrode 41 and opposite electrode 42.

Discharge device 10 may omit opposite electrode 42. In this case, the leader discharge is produced between discharge electrode 41 and a member such as a case present around discharge electrode 41. Further, discharge device 10 may omit both liquid supply unit 5 and opposite electrode 42.

Voltage application circuit 2 may be configured to apply a high voltage between discharge electrode 41 that acts as a positive electrode (plus) and opposite electrode 42 that acts as a negative electrode (ground).

FIG. 3 is only an example of the circuit configuration of discharge device 10, and therefore a specific circuit configuration of voltage application device 1 can be modified as appropriate. For example, voltage application circuit 2 is not limited to the self-excited converter, and may be a separately-excited converter. In voltage application circuit 2, each of transistors Q1, Q2, and Q3 is not limited to the bipolar transistor, and may be a metal-oxide-semiconductor field effect transistor (MOSFET), for example. Furthermore, voltage generation circuit 22 may be configured with a transformer having a piezoelectric element (piezoelectric transformer).

In the comparison between two values such as the monitoring target and the threshold, the expression "not less than" includes both a case in which the two values are equal to each other, and a case in which one of the two values exceeds the other. However, the expression "not less than" herein is not limited thereto, and may have the same meaning as the expression "greater than" that includes only the case in which one of the two values exceeds the other. That is, since it can be arbitrarily modified whether the case in which the two values are equal to each other is included, depending on settings of a threshold and the like, there is no technical difference between the expression "not less than" and the expression "greater than". Similarly, the expression "less than" may have the same meaning as the expression "not more than".

(4) Summary

As described above, voltage application device 1 according to the present exemplary embodiment includes voltage application circuit 2 and control circuit 3. Voltage application circuit 2 is configured to apply a voltage (apply voltage) to load 4 including discharge electrode 41 to cause discharge electrode 41 to discharge. Control circuit 3 is configured to control voltage application circuit 2 based on a monitoring target including at least one of an output current and an output voltage of voltage application circuit 2. Control circuit 3 causes voltage application circuit 2 to alternately repeat a first mode and a second mode. The first mode is a mode that raises the apply voltage while time elapses, and generates a discharge current by promoting corona discharge to dielectric breakdown to generate a discharge current. The second mode is a mode that lowers the apply voltage to cut off the discharge current by causing load 4 to be in an overload state against voltage application circuit 2. Control circuit 3 causes voltage application circuit 2 to operate in the first mode when magnitude of the monitoring target is less than a threshold, and causes voltage application circuit 2 to operate in the second mode when the magnitude of the monitoring target is not less than the threshold.

With this configuration, voltage application circuit 2 operates in the first mode to raise the apply voltage while time elapses until the magnitude of the monitoring target reaches the threshold. At this time, at discharge electrode 41, the corona discharge is promoted to the dielectric breakdown and the discharge current is generated. When the magnitude of the monitoring target reaches the threshold, voltage application circuit 2 operates in the second mode that lowers the apply voltage. At this time, load 4 enters an overload state against voltage application circuit 2 and the discharge current is cut off. As a result, in voltage application device 1 according to the present exemplary embodiment, when the apply voltage is raised and then the dielectric breakdown is generated, a relatively large discharge current instantaneously flows, and immediately after that, the apply voltage is lowered and the discharge current is cut off. Then, the apply voltage is raised and the dielectric breakdown is generated again. Such a phenomenon is repeated. That is, in voltage application device 1, a discharge path is intermittently formed around discharge electrode 41 by leader discharge, thereby repeatedly generating a pulsed discharge current. Although the leader discharge produces about twice to 10 times radicals larger than those in the corona discharge, an amount of ozone generated is suppressed to the same amount as that in the corona discharge. Furthermore, the leader discharge can favorably produce charged fine particulate liquid having radicals, in comparison with a case in which energy to be introduced is merely increased in corona discharge. Accordingly, voltage application device 1 according to the present exemplary embodiment has an advantage in which an amount of ozone generated can be suppressed while increasing an amount of radicals produced.

Furthermore, in voltage application device 1 according to the present exemplary embodiment, control circuit 3 controls voltage application circuit 2 according to a comparison result between the monitoring target and the threshold, thereby achieving the leader discharge. Control circuit 3 in such a configuration can be basically implemented by a circuit configuration similar to a voltage application device for generating the corona discharge. More specifically, when the corona discharge is generated, such control that the control circuit maintains an output voltage or an output current of the voltage application circuit substantially constant may be used. In this case, the control circuit including a voltage control circuit and a current control circuit may be used. Similar to this case, voltage application device 1 according to the present exemplary embodiment uses control circuit 3 including voltage control circuit 31 and current control circuit 32. Even with the circuit configuration, voltage application device 1 according to the present exemplary embodiment can achieve the leader discharge by setting the threshold according to load 4 so as to satisfy a condition that produces the leader discharge. In other words, in voltage application device 1 according to the present exemplary embodiment, the threshold is set such that control circuit 3 switches the mode from the first mode to the second mode at timing when load 4 enters an overload state against voltage application circuit 2, and then a discharge current disappears. Accordingly, voltage application device 1 according to the present exemplary embodiment can achieve the leader discharge depending on the setting of the threshold used in control circuit 3, without making a significant change in the circuit configuration of the voltage application device for generating the corona discharge.

Like the present exemplary embodiment, discharge device 10 preferably includes voltage application device 1 and discharge electrode 41. This configuration can set the threshold according to discharge electrode 41, and can set an optimal threshold that easily produces the leader discharge.

Further, like the present exemplary embodiment, it is preferable that discharge device 10 further includes liquid supply unit 5 for supplying liquid to discharge electrode 41, and therefore the liquid is electrostatically atomized by the discharge. This configuration can produce the charged fine particulate liquid having radicals. Accordingly, a long lifetime of radicals can be achieved in comparison with a case in which only the radicals are emitted into the air alone. Further, the charged fine particulate liquid includes, for example, nanometer-sized particulates, thereby suspending the charged fine particulate liquid over a relatively wide range. However, liquid supply unit 5 is not an essential component for discharge device 10, and may be omitted as appropriate.

Like the present exemplary embodiment, it is preferable that discharge device 10 further includes opposite electrode 42 disposed so as to face discharge electrode 41 via a gap. In this case, discharge device 10 is preferably configured such that the dielectric breakdown is intermittently generated between discharge electrode 41 and opposite electrode 42 by applying an apply voltage between discharge electrode 41 and opposite electrode 42. This configuration can stably generate a discharge path between discharge electrode 41 and opposite electrode 42 in which a discharge current flows after the dielectric breakdown. However, opposite electrode 42 is not an essential component for discharge device 10, and may be omitted as appropriate.

Second Exemplary Embodiment

Figure 5:
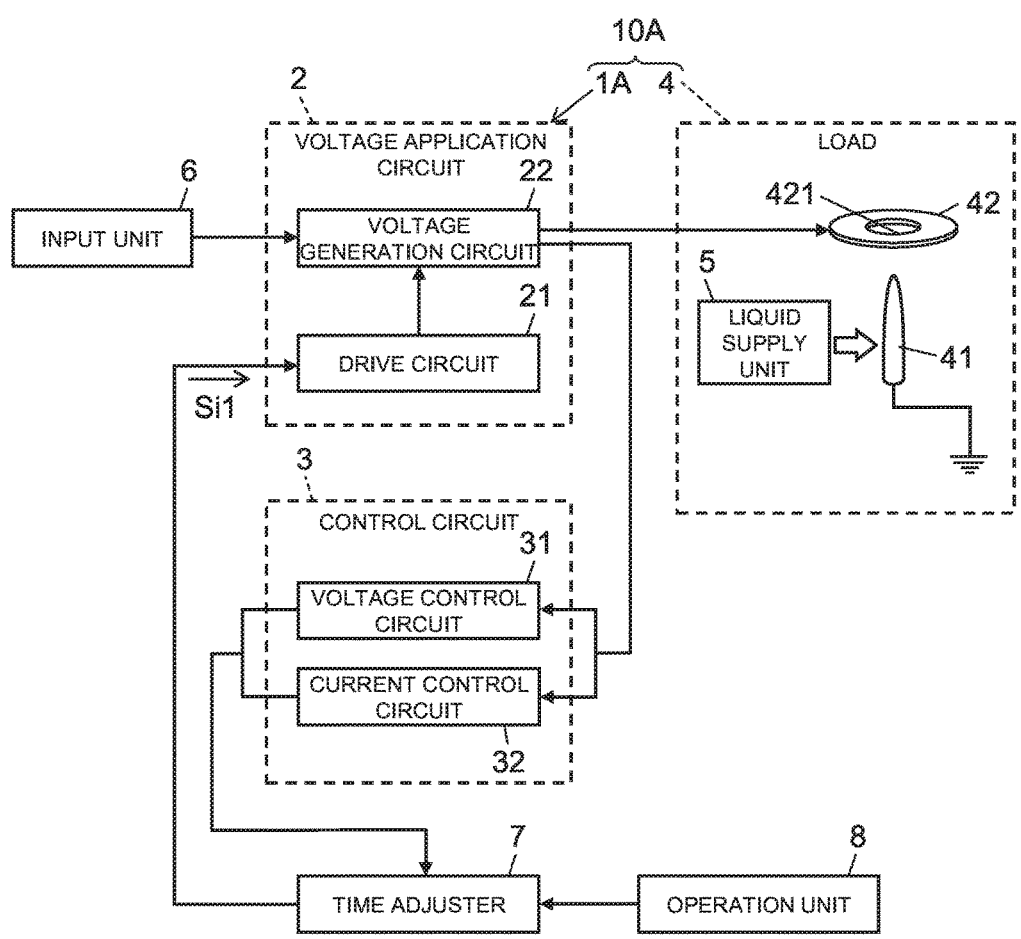
FIG. 5 is a block diagram illustrating a discharge device according to a second exemplary embodiment.

Voltage application device 1A and discharge device 10A according to the present exemplary embodiment are different from voltage application device 1 and discharge device 10 according to the first exemplary embodiment in that time adjuster 7 is further provided as illustrated in FIG. 5. Hereinafter, constituent elements identical to those of the first exemplary embodiment are denoted by like reference signs and explanations thereof will be omitted.

Time adjuster 7 is configured to adjust a length of a discharge period. More specifically, in voltage application device 1A according to the present exemplary embodiment, time adjuster 7 can adjust a length of a period of generation of the dielectric breakdown (discharge period) in the leader discharge in which the dielectric breakdown is intermittently generated.

Incidentally, voltage application circuit 2 includes isolation transformer 220 (refer to FIG. 3). Voltage application circuit 2 is configured to boost input voltage Vin (refer to FIG. 3) that is input to a primary side of isolation transformer 220, and to apply the apply voltage to load 4 that is electrically connected to a secondary side of isolation transformer 220. In the present exemplary embodiment, time adjuster 7 is disposed on the primary side of isolation transformer 220. That is, time adjuster 7 is not disposed in a secondary side circuit connected to secondary winding 222 of isolation transformer 220, but disposed in a primary side circuit connected to primary winding 221 of isolation transformer 220. This configuration is achieved by disposing time adjuster 7 between the output of control circuit 3 and voltage application circuit 2 (drive circuit 21) as illustrated in FIG. 5, for example. More specifically, the control signal is output from control circuit 3 to control voltage application circuit 2. This control signal is input to drive circuit 21 via time adjuster 7, and therefore time adjuster 7 can adjust a time from the cut-off of the discharge current to the dielectric breakdown to adjust the length of the discharge period.

In the present exemplary embodiment, voltage application device 1A further includes operation unit 8 for receiving an operation performed by a user. Time adjuster 7 is configured to adjust the length of the discharge period according to the operation performed by the user to operation unit 8. In other words, in voltage application device 1A, the discharge period can be adjusted manually. The operation to operation unit 8 may be performed during operation of voltage application device 1A (during use), or may be performed on manufacturing voltage application device 1A, for example. When operation unit 8 is operated on manufacturing voltage application device 1A, the user who operates operation unit 8 is a manufacturer of voltage application device 1A.

Next, a specific example of time adjuster 7 will now be described with reference to FIG. 6A and FIG. 6B.

Figure 6A:
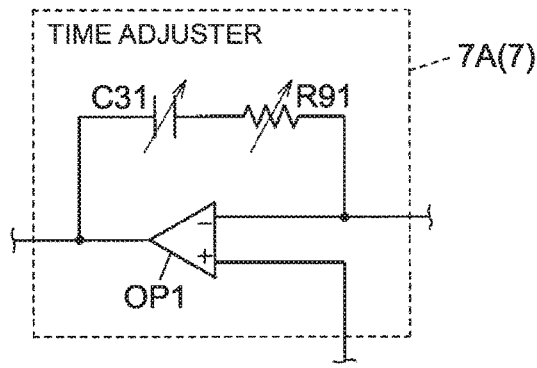
FIG. 6A is a circuit diagram illustrating an example of a time adjuster of the discharge device.

FIG. 6A is an example for using operational amplifier OP1, resister R91, and capacitor C31 in current control circuit 32 as time adjuster 7A. Resister R91 that is a variable resister is provided instead of resister R9 (refer to FIG. 3) in the first exemplary embodiment. Capacitor C31 that is a variable capacitor is provided instead of capacitor C3 (refer to FIG. 3) in the first exemplary embodiment. More specifically, since discharge period T1 is determined by a time constant of an integration circuit including operational amplifier OP1, resister R91, and capacitor C31, discharge period T1 is changed by changing a circuit constant of resister R91 or capacitor C31 (resistance or capacitance).

Figure 6B:
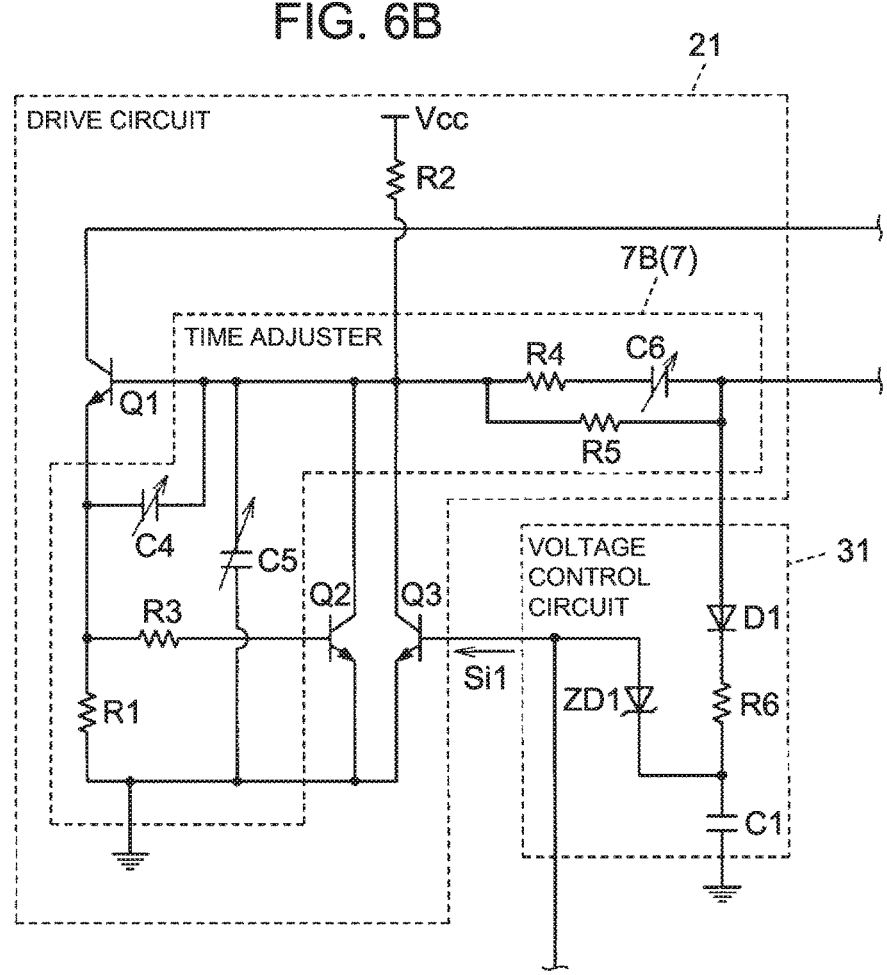
FIG. 6B is a circuit diagram illustrating another example of the time adjuster of the discharge device.

FIG. 6B is an example in which a part of drive circuit 21 is also used as time adjuster 7B. In the example in FIG. 6B, capacitors C4 to C6 are added to drive circuit 21 illustrated in FIG. 3. Each of capacitors C4 to C6 is a variable capacitor. Capacitor C4 is connected between the base and the emitter of transistor Q1. Capacitor C5 is connected between the base of transistor Q1 and the ground. Capacitor C6 is connected to resister R4 in series between both ends of resister R5. In this configuration, a circuit constant of each of capacitors C4 to C6 (capacitance value) can be changed to change discharge period T1.

Figure 7A:
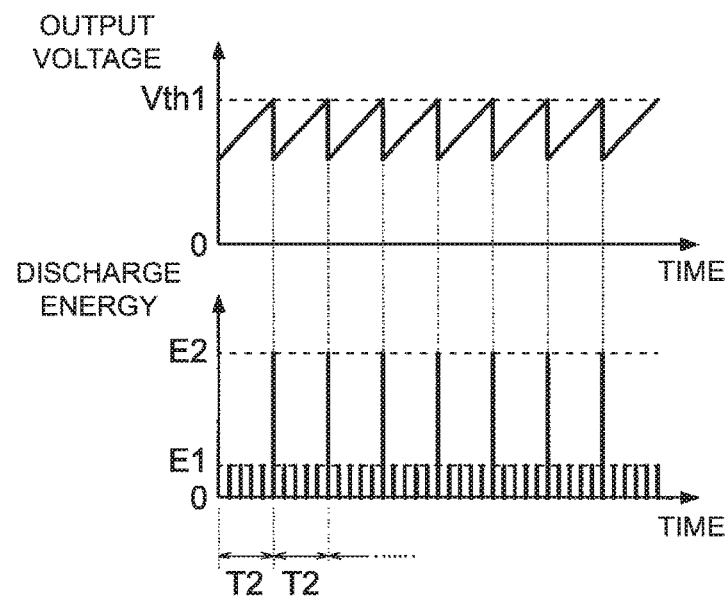
FIG. 7A is a graph schematically illustrating an example of a form of discharge of the discharge device.
Figure 7B:
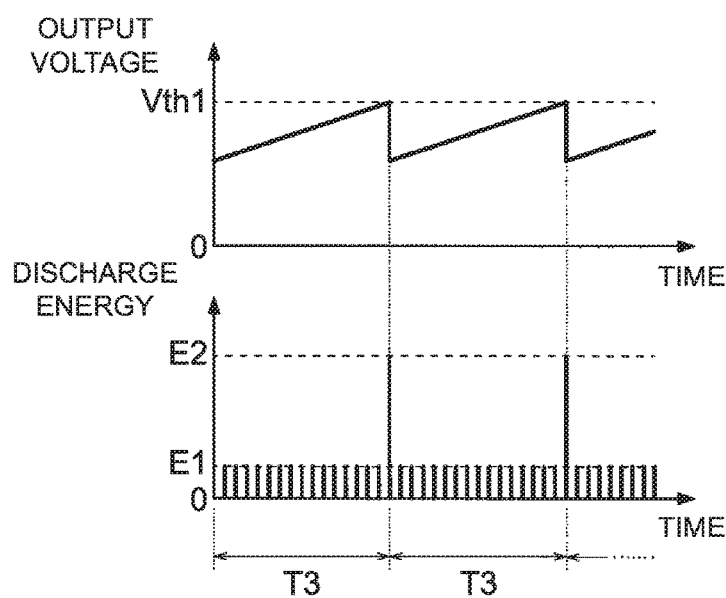
FIG. 7B is a graph schematically illustrating another example of the form of discharge of the discharge device.

In voltage application device 1A configured as described above, time adjuster 7 can adjust the discharge period as illustrated in FIG. 7A and FIG. 7B, for example. In each of FIG. 7A and FIG. 7B, with a horizontal axis representing a time axis, the output voltage of voltage application circuit 2 (apply voltage) is illustrated in an upper stage, and discharge energy is illustrated in a lower stage. When a default discharge period is "T1" (refer to FIG. 2), FIG. 7A illustrates an example in which the discharge period is changed to "T2", and FIG. 7B illustrates an example in which the discharge period is changed to "T3". Herein, "T2" is shorter than "T1", and "T3" is longer than "T1" (T2<T1<T3).

More specifically, when time adjuster 7 adjusts the discharge period so as to be discharge period T2 shorter than the default value (T1), a time interval of generation of the dielectric breakdown becomes shorter and a discharge frequency becomes higher, as illustrated in FIG. 7A. In this case, a time interval of generation of discharge with high energy in which the discharge energy is "E2" (>E1) becomes shorter, and therefore the number of times of generation of discharge with high energy per unit time (for example, one second) increases. As a result, amounts of radicals and ozone produced per unit time can be increased.

On the other hand, time adjuster 7 adjusts the discharge period so as to be discharge period T3 longer than the default value (T1), a time interval of generation of the dielectric breakdown becomes longer and the discharge frequency becomes lower, as illustrated in FIG. 7B. In this case, the time interval of generation of discharge with high energy in which discharge energy is "E2" (>E1) becomes longer, and therefore the number of times of generation of discharge with high energy per unit time (for example, one second) decreases. As a result, the amounts of radicals and ozone produced per unit time can be decreased.

In both a case in which the discharge period is set shorter and a case in which the discharge period is set longer, a ratio between a period in which minute discharge whose discharge energy is equal to "E1" is generated through the corona discharge and a period in which the discharge with high energy is generated in one discharge period is changed. A ratio between amounts of radicals and ozone or the like produced is changed between the period in which the minute discharge is generated and the period in which the discharge with high energy is generated. Accordingly, in both the case in which the discharge period is set shorter and the case in which the discharge period is set longer, a breakdown of components generated by discharge device 10A (radicals, ozone, or the like) is changed.

As described above, voltage application device 1A according to the present exemplary embodiment further includes time adjuster 7 for adjusting the length of the discharge period, and the dielectric breakdown is periodically generated at the discharge period. This configuration causes time adjuster 7 to change the length of the discharge period and to change discharge characteristics of discharge device 10A, thereby adjusting the amount of radicals produced and the breakdown or the like of components generated in discharge device 10.

Like the present exemplary embodiment, it is preferable that voltage application circuit 2 includes isolation transformer 220, boosts input voltage Vin that is input to the primary side of isolation transformer 220, and applies the apply voltage to load 4 that is electrically connected to the secondary side of the isolation transformer 220. In this case, time adjuster 7 is preferably disposed on the primary side of isolation transformer 220. This configuration eliminates a high-voltage capacitor and the like for adjusting the length of the discharge period on the secondary side of isolation transformer 220, thereby miniaturizing circuit elements configuring voltage application device 1A. However, this configuration is not essential for voltage application device 1A, and time adjuster 7 may be disposed on the secondary side of isolation transformer 220.

Like the present exemplary embodiment, it is preferable that voltage application device 1A further includes operation unit 8 for receiving the operation performed by a user, and time adjuster 7 is configured to adjust the length of the discharge period according to the operation performed by the user to operation unit 8. With this configuration, the user can manually adjust the length of the discharge period, thereby freely changing the discharge characteristics depending on an application and a condition of discharge device 10A. However, this configuration is not essential for voltage application device 1A, and operation unit 8 may be omitted as appropriate.

Hereinafter, modifications of the second exemplary embodiment will be listed.

Resister R91 is not limited to the variable resister. A configuration that includes a plurality of resisters and a switch, and switches a connection relationship of the plurality of resisters using the switch may be used. Similarly, each of capacitor C31 and capacitors C4 to C6 are not limited to the variable capacitor. A configuration that includes a plurality of capacitors and a switch, and switches a connection relationship of the plurality of capacitors using the switch may be used.

Time adjuster 7 is not limited to the configuration that changes the discharge period by changing the circuit constant, and may change the discharge period using, for example, a microcomputer. More specifically, when control circuit 3 includes the microcomputer, the function of time adjuster 7 is achieved by changing a duty ratio of a pulse width modulation (PWM) signal output from the microcomputer, for example.

The configuration described in the second exemplary embodiment (including the modifications) can be applicable by combining with the configuration described in the first exemplary embodiment (including the modifications) as appropriate.

Third Exemplary Embodiment

Figure 8:
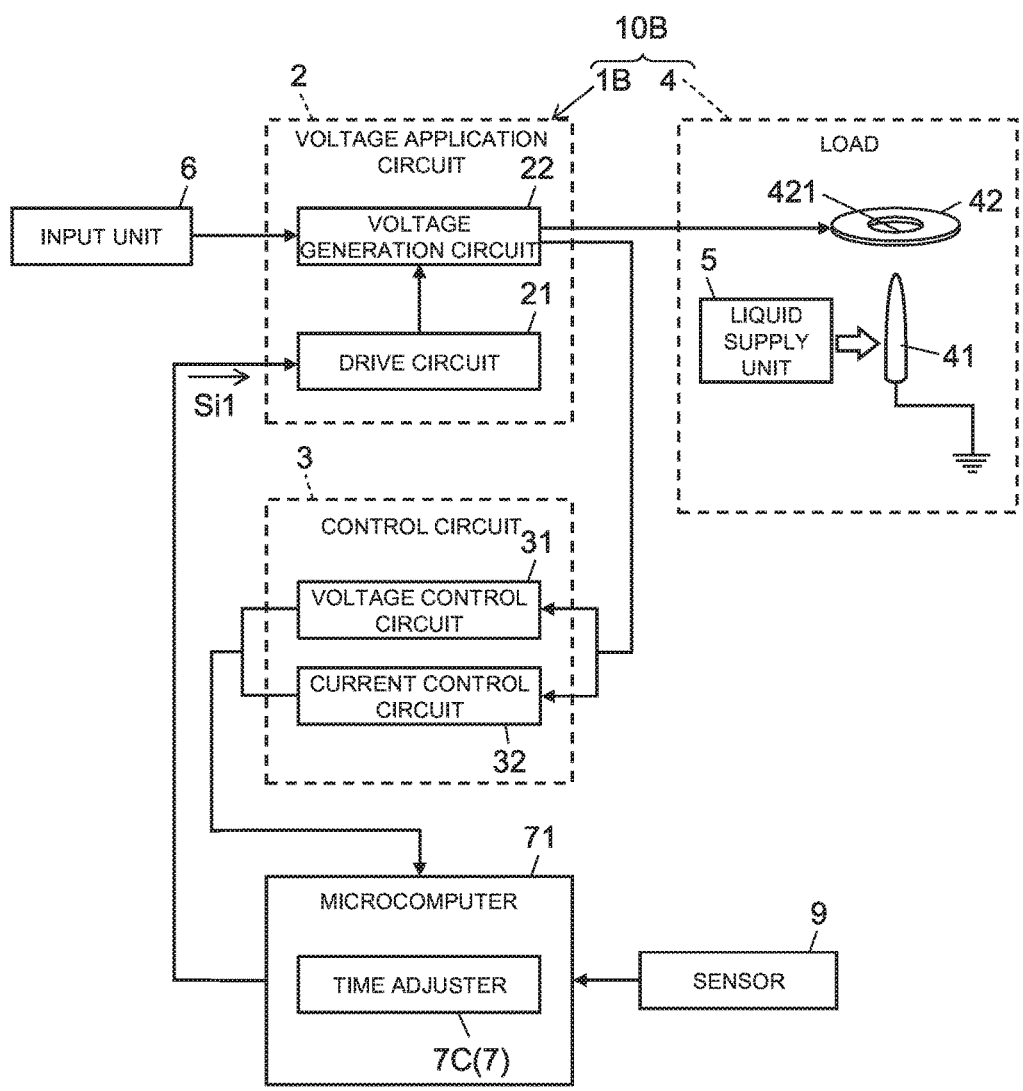
FIG. 8 is a block diagram illustrating a discharge device according to a third exemplary embodiment.

Voltage application device 1B and discharge device 10B according to the present exemplary embodiment are different from voltage application device 1A and discharge device 10A according to the second exemplary embodiment in that time adjuster 7 automatically adjusts the length of the discharge period, as illustrated in FIG. 8. Hereinafter, constituent elements identical to those of the second exemplary embodiment are denoted by like reference signs and explanations thereof will be omitted.

In the present exemplary embodiment, time adjuster 7 is configured to adjust the length of the discharge period according to an output of sensor 9. Sensor 9 detects a condition around discharge electrode 41. Sensor 9 detects information on environment (condition) around discharge electrode 41, such as a temperature, humidity, an odor index, illuminance, and presence of a person around discharge electrode 41. The present exemplary embodiment will be described such that voltage application device 1B includes sensor 9 as its component, but voltage application device 1B my not include sensor 9 as its component.

More specifically, time adjuster 7 is implemented as one function of microcomputer 71 connected to sensor 9. That is, voltage application device 1B includes microcomputer 71. Microcomputer 71 obtains the output of sensor 9 (hereinafter, also referred to as "sensor output"), and operates as time adjuster 7C that adjusts the length of the discharge period according to the sensor output.

Hereinafter, several specific examples of operation for adjusting the discharge period performed by time adjuster 7C will be described.

As a first example, when humidity around discharge electrode 41 is not less than a prescribed value, time adjuster 7C sets the discharge period to discharge period T2 that is shorter than the default value (refer to FIG. 7A), and therefore the amounts of radicals and ozone produced per unit time are increased. Therefore, for example, under the environment in which the humidity is high and an odor easily fills therein, discharge device 10B increases the amount of radicals produced, and therefore deodorization (odor elimination) can be effectively performed.

As a second example, when the humidity around discharge electrode 41 is not less than the prescribed value, time adjuster 7C sets the discharge period to discharge period T3 that is longer than the default value (refer to FIG. 7B). Therefore, for example, under the environment in which the humidity is high and an odor easily fills therein, components (radicals, ozone, or the like) generated by discharge device 10B are changed, and therefore deodorization (odor elimination) can be effectively performed.

As a third example, when a person present around discharge electrode 41, time adjuster 7C sets the discharge period to discharge period T2 that is shorter than the default value (refer to FIG. 7A), and therefore the amounts of radicals and ozone generated per unit time are increased. Therefore, for example, while a person is not present near discharge device 10B, the amount of radicals produced can be suppressed, thereby suppressing consuming power of discharge device 10B.

As described above, in voltage application device 1B according to the present exemplary embodiment, time adjuster 7 is configured to automatically adjust the length of the discharge period according to the output of sensor 9 that detects the condition around discharge electrode 41. With this configuration, voltage application device 1B can automatically achieve optimal discharge characteristics according to the condition around discharge electrode 41.

The configuration described in the third exemplary embodiment can be applicable by combining with the configuration described in the first exemplary embodiment (including the modifications) or the second exemplary embodiment (including the modifications) as appropriate.

A voltage application device and a discharge device are applicable to various applications including a refrigerator, a washing machine, a hair dryer, an air conditioner, a fan, an air cleaner, a humidifier, a facial treatment device, and an automobile.

What is claimed is:

1. A voltage application device electrically connected to a discharge electrode and an opposite electrode, the opposite electrode being disposed so as to face the discharge electrode via a gap, the voltage application device comprising:
    a voltage application circuit configured to apply a voltage to a load including the discharge electrode and the opposite electrode to cause the discharge electrode to perform a discharge; and
    a control circuit configured to control the voltage application circuit, based on a monitoring target including at least one of an output current and an output voltage of the voltage application circuit,
    wherein the control circuit causes the voltage application circuit to alternately repeat a first mode that raises the voltage while time elapses, and generates a discharge current by promoting corona discharge to dielectric breakdown, the dielectric breakdown being generated between the discharge electrode and the opposite electrode, and a second mode that lowers the voltage to cut off the discharge current by causing the load to be in an overload state against the voltage application circuit, and
    the control circuit causes the voltage application circuit to operate in the first mode when magnitude of the monitoring target is less than a threshold, and causes the voltage application circuit to operate in the second mode when the magnitude of the monitoring target is not less than the threshold.

2. The voltage application device according to claim 1, further comprising
    a time adjuster configured to adjust a length of a discharge period,
    wherein the dielectric breakdown is periodically generated at the discharge period.

3. The voltage application device according to claim 2, wherein
    the voltage application circuit includes an isolation transformer, and is configured to boost an input voltage that is input to a primary side of the isolation transformer and to apply the voltage to the load that is electrically connected to a secondary side of the isolation transformer, and
    the time adjuster is disposed on the primary side of the isolation transformer.

4. The voltage application device according to claim 2, further comprising
    an operation unit configured to receive an operation performed by a user,
    wherein the time adjuster is configured to adjust the length of the discharge period in accordance with the operation performed by the user to the operation unit.

5. The voltage application device according to claim 2, wherein the time adjuster is configured to automatically adjust the length of the discharge period in accordance with an output of a sensor that detects a condition around the discharge electrode.

6. A discharge device comprising:
the voltage application device according to claim 1; and
the discharge electrode.

7. The discharge device according to claim 6, further comprising
a liquid supply unit configured to supply liquid to the discharge electrode,
wherein the liquid is electrostatically atomized by the discharge.

8. The discharge device according to claim 6, further comprising
the opposite electrode,
wherein the dielectric breakdown is intermittently generated between the discharge electrode and the opposite electrode.

* * * * *